United States Patent [19]

Bashkansky et al.

[11] Patent Number: 5,418,797

[45] Date of Patent: May 23, 1995

[54] TIME GATED IMAGING THROUGH SCATTERING MATERIAL USING POLARIZATION AND STIMULATED RAMAN AMPLIFICATION

[75] Inventors: Mark Bashkansky; John F. Reintjes, both of Alexandria, Va.

[73] Assignee: The United States of America as represented by the Secretary of the Navy, Washington, D.C.

[21] Appl. No.: 3,999

[22] Filed: Jan. 15, 1993

[51] Int. Cl.$^6$ ............................ A61B 6/00; G01J 3/44
[52] U.S. Cl. ...................................... 372/3; 128/665; 128/664; 128/633; 356/301
[58] Field of Search ........................... 372/3; 356/301; 128/633, 664, 665

[56] References Cited

U.S. PATENT DOCUMENTS

| | | | |
|---|---|---|---|
| 3,802,777 | 4/1974 | Regnier et al. | 356/75 |
| 4,178,079 | 12/1979 | Bjorklund et al. | 350/353 |
| 4,193,690 | 3/1980 | Levenson et al. | 356/301 |
| 4,270,864 | 6/1981 | Barrett et al. | 356/301 |
| 4,277,760 | 7/1981 | Eckbreth | 331/94.5 |
| 4,405,237 | 10/1983 | Manvccia et al. | 356/301 |
| 4,512,660 | 4/1985 | Goldberg | 356/301 |
| 4,945,239 | 7/1990 | Wist et al. | 250/358.1 |
| 5,275,168 | 1/1994 | Reintjes et al. | 128/665 |
| 5,303,710 | 4/1994 | Bashkansky et al. | 128/665 |

FOREIGN PATENT DOCUMENTS 0191946  8/1988  Japan .

OTHER PUBLICATIONS

Duncan et al., "Time–Gated Imaging through Scattering Media Using Stimulated Raman Amplification". Optics Letters, 12-1-91, vol. 16, No. 23, 1868–1870.
Levenson, "Introduction to Nonlinear Laser Spectroscopy", Academic Press, 1982, Sec. 4.6, pp. 139–145 no month available.

Primary Examiner—Rodney B. Bovernick
Assistant Examiner—Robert McNutt
Attorney, Agent, or Firm—Thomas E. McDonnell; Daniel Kalish

[57] ABSTRACT

An apparatus for imaging through scattering materials produces a broadband laser reference beam and a correlated Stokes illumination beam. The broadband reference beam has a preselected Raman pump wavelength and the Stokes illumination beam has a preselected Stokes wavelength. The Stokes illumination beam is transmitted into the scattering material to obtain a Stokes signal beam having a first image carrying component and a first nonimage component. A relative delay is produced between the reference beam and the Stokes signal beam. The delayed reference beam and the delayed Stokes signal beam are polarized. The polarized reference beam and the polarized Stokes signal beam are combined to produce a combined beam having a Stokes component and a reference component, the Stokes component having a second image carrying component and a second nonimage component, so that the second image carrying component and the reference component are mutually correlated, and so that the polarization state of the Stokes component differs from the polarization state of the reference component. A Stimulated Raman amplifier responsive to the combined beam produces an amplified signal beam having a third image carrying component with polarization state perpendicular to the polarization state of the Stokes component and having a third nonimage component with polarization state parallel to the polarization state of the Stokes component. The third image carrying component is separated from the rest of the amplified signal beam with the use of a polarizer and is later detected.

14 Claims, 3 Drawing Sheets

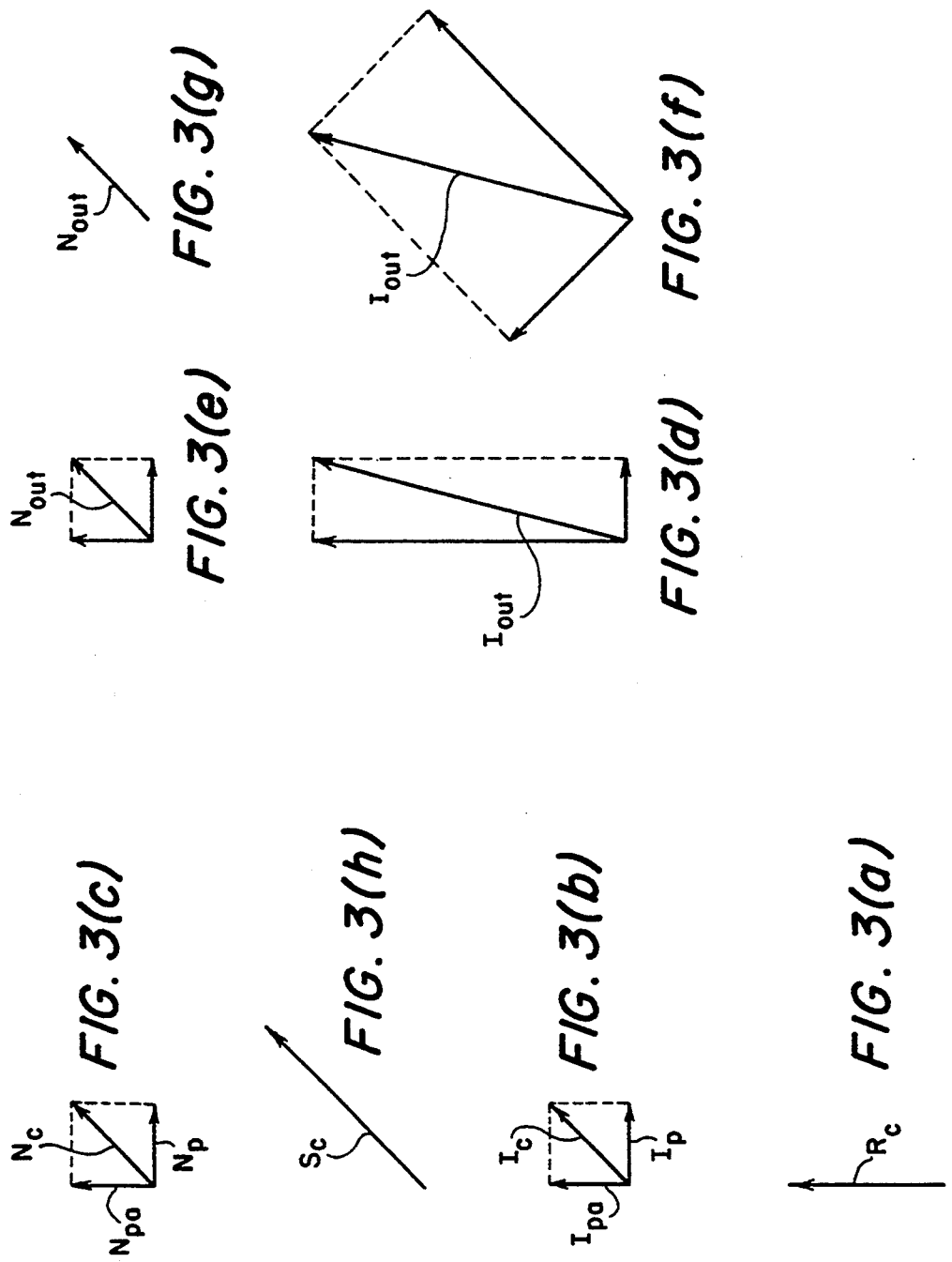

TIME GATED IMAGING THROUGH SCATTERING MATERIAL USING POLARIZATION AND STIMULATED RAMAN AMPLIFICATION

CROSS-REFERENCE TO RELATED APPLICATIONS

This application is related to commonly assigned, U.S. application Ser. No. 07/861,213, filed on Mar. 31, 1992, U.S. Pat. No. 5,275,168 on Jan. 1, 1994, by Reintjes, Duncan, Mahon, Tankersly, Waynant and Bashkansky and entitled "Time-Gated Imaging Through Dense-Scattering Materials Using Stimulated Raman Amplification," to commonly assigned, U.S. application Ser. No. 07/970,886, filed on Nov. 3, 1992, U.S. Pat. No. 5,303,710 on Apr. 19, 1994, by Bashkansky and Reintjes and entitled "Apparatus for Imaging an Object in or Through a Scattering Medium Using Coherent Anti-Stokes Raman Scattering," and to commonly assigned, U.S. application Ser. No. 07/983,334, filed on Dec. 30, 1992. U.S. Pat. No. 5,270,853 on Dec. 14, 1993, by Bashkansky and Reintjes and entitled "Method and Apparatus for Imaging an Object in or Through a Scattering Medium by Using Multiple-Wave Mixing."

1. Field of the Invention

The present invention relates to imaging devices, and more particularly to a system using polarization optics and coherently amplified Stimulated Raman amplification for the time-gated examination of objects that are part of, embedded in, or viewed through scattering materials.

2. Description of the Related Art

Images of objects that are part of, embedded in, or viewed through a medium in which a significant amount of multiple path scattering occurs are usually blurred or otherwise degraded in resolution or completely obscured because the different paths over which the scattered radiation travels causes the image to appear to arise from more than one location within the scattering medium. There are several methods that can be used to overcome this problem, with each having certain disadvantages.

A first method involves the spatial filtering of the image to include only those rays that are not deviated too far from the axis of the optical system. The limitations of this first method occur because the spatial frequencies of the scattered radiation can overlap those required to form the image of the object. Either the resolution with which the object can be imaged is limited, or the scattered radiation cannot be filtered out effectively.

A second method of overcoming the blurring of the image is to time gate the transmitted signal so that only the earliest light that emerges from the scattering medium is recorded by a detector. This "first light" either is not scattered, or is scattered over a relatively short path compared to light that emerges later, and therefore provides the least amount of image degradation. The degree of improvement provided by this second method depends on the length of the scattering path over which the detected signal is integrated, which, in turn, is determined directly by the duration of the time gate. In general, the shorter the time gate, the better the image, down to some characteristic time that is determined by the scattering characteristics of the medium. Imaging through dense scattering materials, such as biological tissue, or solids or liquids that appear translucent or even opaque to the unaided eye can require gating times of the order of 10 picoseconds or less.

There are several techniques currently used to perform such time-gated imaging measurements, including various forms of electronic gating and optical gating. Electronic gating can be accomplished either by gating a photoelectric image tube directly, or by switching some other part of the photoelectric detection circuit. These techniques are currently limited to gating times of the order of 50–100 picoseconds (psec) or longer, corresponding to minimum scattering paths of the order of 1.5–3 centimeters (cm) by the limitations of available electronic switching devices.

Another technique involves the use of picosecond or femtosecond pulses for illumination of the object, followed by an optical gating technique to provide the time resolution. Such techniques can provide time gates in the picosecond or subpicosecond regime, depending on the length of the optical pulse. For comparison with electronic gating methods, a time gate of 100 femtoseconds corresponds to a scattering path of 0.003 cm.

One gating technique suitable for picosecond or femtosecond pulses is holography, in which the image is detected only by a coincidence between the illumination pulse and a reference pulse of the desired length. Conventional holography, in which the image is recorded on high resolution photographic film, requires a substantial amount of light in the transmitted signal to interfere with the reference pulse to establish the holographic record. It thus limits the extinction in the sample that can be accommodated. Electronic holography, in which the fringes are detected with a sensitive two-dimensional camera and the hologram is reconstructed through computer analysis, overcomes the sensitivity problem, allowing greater attenuation in the sample. However, all of the transmitted light is recorded at the detector. If a large fraction of the transmitted light is contained in the non-image carrying tail that is delayed through scattering, the interference fringes that form the hologram will be washed out, and the noise in the image will be increased until the image is totally obscured.

Holography can also be accomplished with broadband, long-pulse laser light, in which the gate time is determined by the inverse of the bandwidth of the light. This approach provides subpicosecond gate times without the need for subpicosecond technology. However, as it has been applied to date, it suffers from the same disadvantages described above for picosecond holography: large signal requirements and relatively low contrast between the image carrying portion of the transmitted light and the non-image carrying tail.

Another technique for short pulse gating is the use of a Kerr shutter, in which the transmission of light through a cell between crossed polarizers is controlled by a second pulse of light. The gate times for this approach can be of the order of picoseconds, depending on the duration of the controlling light pulse and the response time of the active medium in the Kerr gate. This technique suffers from limitations in contrast because of leakage of the wrong polarization through the polarizers, and losses in the Kerr gate because the transmission is less than 100%. Contrast can be increased by cascading gates, but only at the expense of overall transmission. The loss of transmission can be especially detrimental for viewing through highly attenuating samples in which there is a limit on allowable irradiation levels, such as for living tissue.

Image amplification with picosecond time-gated amplifiers have also been described in the prior art. These amplifiers have been based on dye amplifiers pumped by picosecond laser pulses. By themselves the dye amplifiers have relaxation times of the order of several nanoseconds and, therefore, gating times of the same order of magnitude. Picosecond gating times were achieved by raising the dye concentration and pumping level to such a degree that substantial radiation from the upper laser level occurs, leading to population "dumping" and reduced lifetime of the upper state. The limitations of these amplifiers are that the high level of fluorescence necessary to produce the short gating time contributes a background on top of the amplified image, limiting the sensitivity and increasing the noise level. The amplifiers have had gains of only 100 to 1000, limiting the degree of contrast with the delayed light. Finally, fundamental considerations of the noise level of amplifiers show that the minimum noise level occurs when the time-bandwidth product $\Delta\nu\Delta t = 1$. The dye fluorescence is radiated over the full bandwidth of the dye amplifier, of the order of 500 cm$^{-1}$. As a result, for gating times of the order of 10 picoseconds, the time-bandwidth product is in excess of 100, increasing the minimum noise value by the same factor.

Several other techniques are also possible. Streak cameras can be used to record the image. Time resolutions down to 2 picoseconds are currently possible. However, only a one-dimensional image is obtained, requiring scanning to produce a two-dimensional image. In addition, the streak cameras are of limited sensitivity, limiting their utility in detecting low-level signals. Another approach that uses time-gating involves the technique of four-wave mixing. In this approach the signal beam impinges on a non-linear medium that is being irradiated with co-propagating picosecond light pulses. Conversion of the signal light takes place only while the gating pulse is present. The main drawback to this approach is the combination of low conversion efficiencies associated with the conversion process (10% or less), coupled with limitations on the allowable illumination signal as set by the ANSI standards for irradiation of living tissue. Four-wave mixing using phase conjugation has also been suggested. The disadvantage of this technique is that, while phase conjugation can correct refractive distortion, it does not correct for scattering distortion due to fundamental considerations.

Non time-gating techniques also include the use of holographic recordings using spatial correlation to discriminate against the non-image light. This approach has the same limitations due to low contrast with non-correlated light as discussed above for holography. Finally, use may be made of absorption in the sample to attenuate the longer paths associated with the multiple scattered light. This can work in materials that are highly absorbing, but not for materials that are primarily scattering rather than absorbing.

A related Raman interaction that has not been used for time gating, and is impractical for time-gated imaging, is Raman Induced Kerr effect Spectroscopy (RIKES). In this interaction, two narrow band beams are used: a pump beam at a fixed wavelength, and a probe beam that is varied in wavelength near a Raman resonance. In the RIKES interaction, birefringence is induced in the material by the pump intensity and the polarization of the probe is changed. The probe is detected through crossed polarizers and the variation of its intensity as its wavelength is tuned through the Raman resonance provides the spectroscopic information.

SUMMARY OF THE INVENTION

It is an object of the invention to provide optical examination of objects that are part of, embedded in or viewed through scattering materials with the use of time-gating.

Another object of the invention is to provide time-gated imaging of objects that are part of, embedded in or viewed through scattering media using polarization optics and Stimulated Raman amplification.

A further object of the invention is to provide time-gated imaging of objects that are part of, embedded in or viewed through scattering media using polarization optics, Stimulated Raman amplification and a short pulse broadband stochastic illumination beam.

Another object of the invention is to provide time-gated imaging of objects that are part of, embedded in or viewed through scattering media using polarization optics, Stimulated Raman amplification and a limited energy broadband stochastic illumination beam.

Another object of the invention is to provide direct, two-dimensional imaging of objects that are part of, embedded in or viewed through scattering materials with a high degree of contrast of up to $10^{10}$ with non-image light, by using polarization optics and Stimulated Raman amplification of image carrying light.

A further object of the invention is to provide an apparatus and method for the direct time-gated imaging of biological tissue by using Stimulated Raman amplification with picosecond time resolution.

These and other objectives are achieved by an apparatus for imaging into or through scattering materials. The apparatus includes a source for producing a broadband laser reference beam and a Stokes illumination beam correlated to the reference beam, the broadband reference beam having a center wavelength at a preselected Raman pump wavelength and the Stokes illumination beam having a center wavelength at a preselected Stokes wavelength. The Stokes illumination beam is transmitted into the scattering material to obtain a Stokes signal beam having a first image carrying component and a first nonimage component. Means responsive to the reference beam produce a delayed reference beam and means responsive to the Stokes signal beam produce a delayed Stokes signal beam having a second image carrying component and a second nonimage component functionally dependent on the first nonimage component, so that the delayed reference beam and the second image carrying component of the delayed Stokes signal beam differ by a preselected time-differential. The delayed reference beam is polarized, and the delayed Stokes signal beam is polarized, the polarized Stokes signal beam having a polarized image carrying component and a polarized nonimage component. The polarized reference beam and the polarized Stokes signal beam are combined to produce a combined beam having a Stokes component and a reference component, the Stokes component having a third image carrying component and a third nonimage carrying component, so that the third image carrying component and the reference component are mutually correlated, and so that the polarization state of the Stokes component differs from the polarization state of the reference component.

A Stimulated Raman amplifier responsive to the combined beam produces an amplified signal beam having a fourth image carrying component with polarization state perpendicular to the polarization state of the Stokes component and having a fourth nonimage component with polarization state parallel to the polarization state of the Stokes component. The fourth image carrying component is separated from the rest of the amplified signal beam with the use of a polarizer and is subsequently detected.

BRIEF DESCRIPTION OF THE DRAWINGS

These and other objects, features and advantages of the invention, as well as the invention itself, will become better understood by reference to the following detailed description when considered in connection with the accompanying drawings wherein like reference numerals designate identical or corresponding parts throughout the several views, and wherein:

FIGS. 3(a)-3(h) show polarization states (not to scale) useful in understanding the operation of the invention.

DETAILED DESCRIPTION OF THE PREFERRED EMBODIMENT

Figure 1:
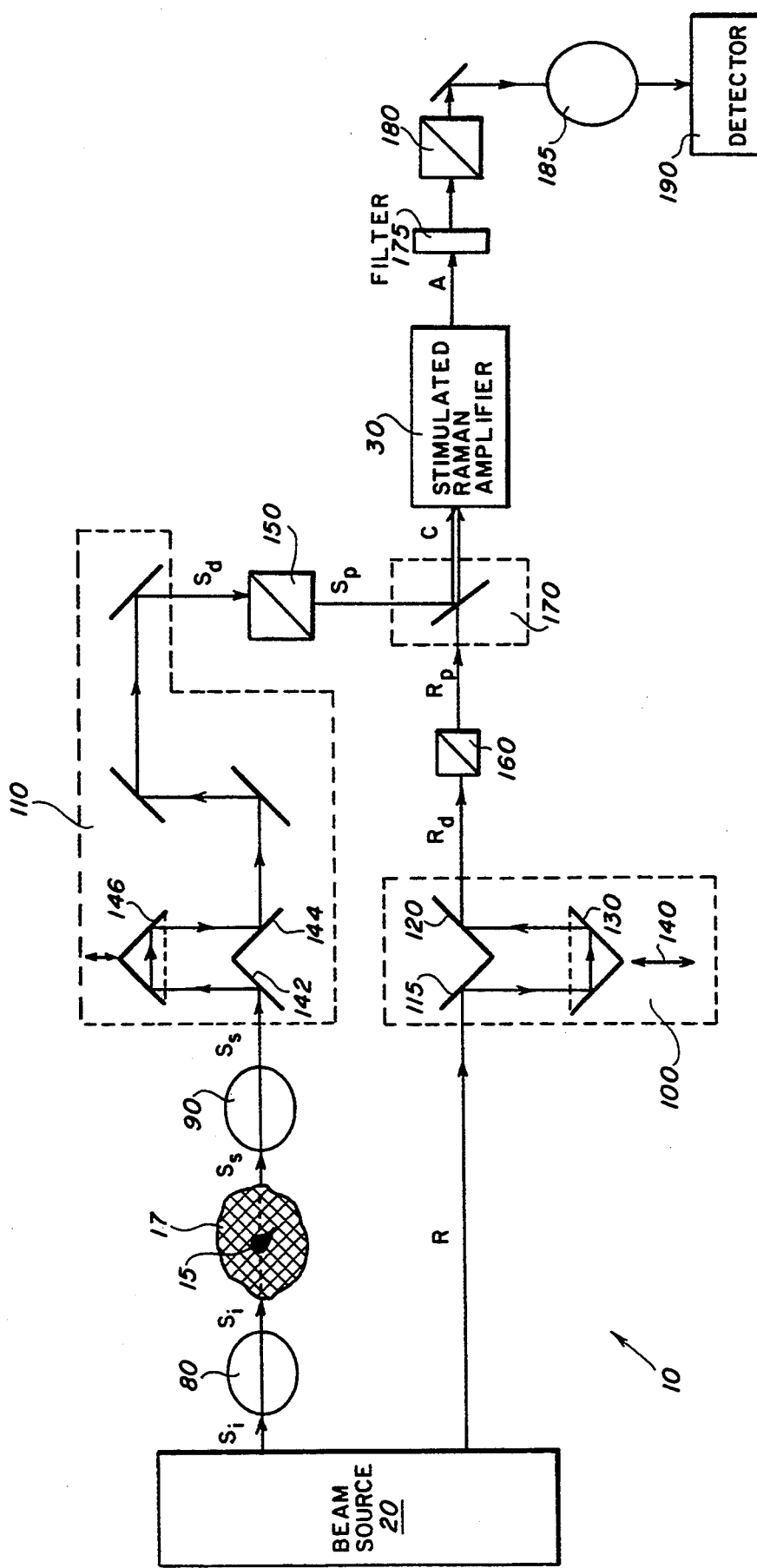
FIG. 1 is a schematic block diagram of a preferred embodiment of the invention.

Referring now to the drawings, FIG. 1 shows a system 10 according to the invention for the detection and examination of one or more objects 15 which, if present, are part of, embedded in, or viewed through scattering material 17. Examples of objects that can be imaged by this invention include resolution charts viewed through several centimeters of scattering material such as milk and raw meat, needles and pins either viewed through or embedded in scattering materials, and tumors in soft tissue. It is expected that the invention will be useful in detecting and examining tumors in soft biological tissue, and in detecting and examining industrial contaminants.

The object 15 may be as small as a single molecule, or occupy as much space as the entire scattering material 17. Regardless, the object 15 must be optically distinct from the scattering material 17 with respect to Stokes light illuminating the scattering material 17, as discussed later. The imaging system 10 will produce an image (not shown) of the scattering material 17, which image is indicative of the presence or absence of the object 15. If the object 15 is present in the scattering material 17, the image contains information about the object 15.

A beam source 20 produces a broadband reference beam R and a Stokes illumination beam $S_i$ that is, as explained later, amplitude and phase correlated to the reference beam R. The reference beam R has a center wavelength at a preselected Raman pump wavelength $\lambda_p$ and the Stokes illumination beam $S_i$ has center wavelength at a preselected Stokes wavelength $\lambda_S$. As explained later, a Stimulated Raman amplifier 30 is pumped at pump wavelength $\lambda_p$ to amplify a signal of Stokes wavelength $\lambda_S$.

The degree of correlation between the reference beam R and the Stokes illumination beam $S_i$ is given by the normalized field correlation function $$\rho'(R, S_i) = \qquad (1)$$

$$\text{MAX}_p \left[ \frac{|\int A_R(t) \cdot A^*_{S_i}(t - \tau) dt|^2}{\int A_R(t) \cdot A^*_R(t) dt \int A_{S_i}(t - \tau) \cdot A^*_{S_i}(t - \tau) dt} \right],$$

where $A_R$ and $A_{S_i}$ are the complex amplitudes of the reference and Stokes illumination beams R and $S_i$, respectively, and $\tau$ is a delay constant with value chosen to maximize the expression within the brackets. The value of $\rho'$ (Eqn. 1) varies from 0 for completely uncorrelated beams to 1 for perfectly correlated beams. For coherent beams containing pulses, complete correlation $(\rho' = 1)$ consists of overlap between the envelopes of the pulses in each beam. For broad band stochastic radiation, complete correlation $(\rho' = 1)$ occurs when the phase and amplitude variations in one beam are reproduced in the other beam, and the amplitude and phase structure of one beam coincides with the corresponding amplitude and phase structure in the other beam. While this invention will work at some level with any degree of correlation $\rho'$ between reference beam R and Stokes illumination beam $S_i$, the performance improves as the value of $\rho'$ approaches unity. A correlation function $\rho'$ of unity is attained when the Stokes illumination beam $S_i$ is proportional to the reference beam R, that is, $$A_{S_i} e^{i\phi_{S_i}} = k A_R \cdot e^{i\phi_R}, \qquad (2)$$

where $\phi_{S_i}$ and $\phi_R$ are the phases of the Stokes illumination beam $S_i$ and the reference beam R, respectively.

The amplitude and phase correlation $\rho$ of signals D and R, unadjusted for delay, is $$\rho(R,D) = \frac{|\int A_R(t) \cdot A^*_D(t) dt|^2}{\int A_R(t) \cdot A^*_R(t) dt \int A_D(t) \cdot A^*_D(t) dt}, \qquad (3)$$

where $A_R$ and $A_D$ are the complex amplitudes of the reference and Stokes illumination beams R and D, respectively.

Reference beam R is typically a laser pulse beam with pulse duration or bandwidth chosen for optimal gate time. The coherence time $\Delta t_c$ of such a pulse beam should be at most that gate time. This condition will be satisfied by a coherent pulse with duration of at most that gate time. This condition will also be satisfied by a relatively long stochastic pulse of sufficiently broad bandwidth so that the coherence time $\Delta t_c$ is at most that gate time, since the pulse duration is the gate time. Such a broadband pulse may be thought of as a superposition of component pulses, each component pulse being coherent and having pulse duration of at most $\Delta t_c$, and having random phase with respect to the other component pulses. For imaging into or through biological material, the optimal gate time is typically in the range 0.1 picoseconds (psec) to 30 psec, and the pump wavelength $\lambda_p$ is in the range 400 nanometers (nm) to 1 micrometer ($\mu$m).

Figure 2:
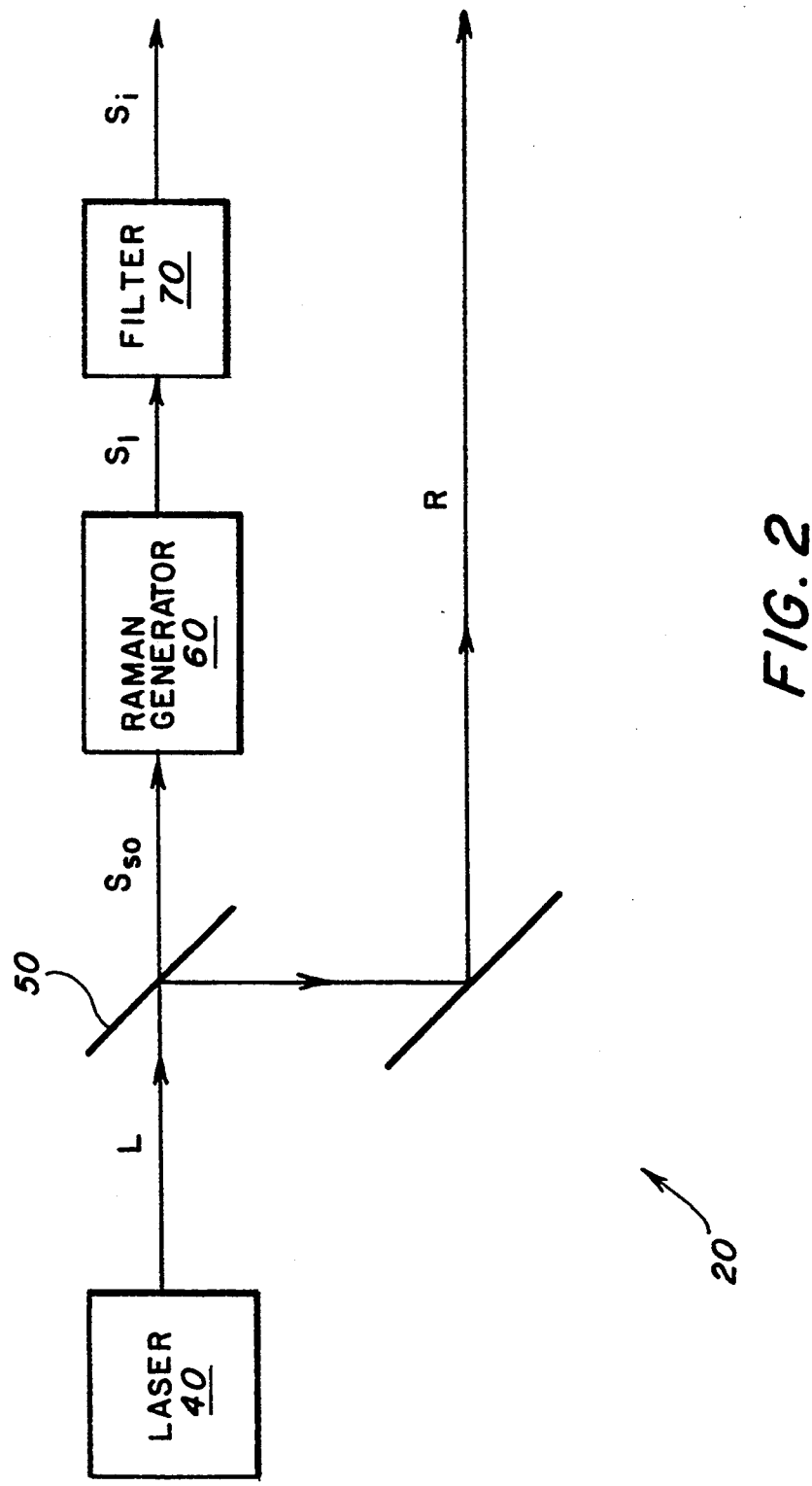
FIG. 2 is a schematic block diagram of an exemplary beam source 20 of the embodiment of FIG. 1.

Referring now to FIG. 2, an exemplary beam source 20, which produces reference beam R and Stokes illumination beam $S_i$ with high amplitude and phase correlation $\rho'(R,S_i)$ (Eqn. 1) is shown. As shown in FIG. 2, a laser 40 or other source of coherent light produces laser light L with wavelength $\lambda_p$. A beam-splitter 50 divides light L into a reference beam R and a Stokes source beam $S_{so}$ so that the reference beam R and the Stokes source beam $S_{so}$ propagate along separate paths. Both the reference beam R and the Stokes source beam $S_{so}$ have wavelength $\lambda_p$.

The Stokes source beam $S_{so}$ enters a Raman generator 60 which contains a Raman generator material (not shown). In response to the interaction of the Raman generator material with this Stokes source beam $S_{so}$ of wavelength $\lambda_p$, the Raman generator 60 produces light that is shifted in wavelength from the pump wavelength $\lambda_p$ by an amount corresponding to the Raman shift of the Raman generator material contained in the Raman generator 60. As a result of this shift, the Raman generator 60 produces Stokes light $S_l$ which has a Raman-shifted component of wavelength $\lambda_s$, and an unshifted component of wavelength $\lambda_p$.

The Stokes light $S_l$ passes to a filter 70 which transmits the component of Raman-shifted wavelength $\lambda_s$ light therethrough and blocks the light at the unshifted wavelength $\lambda_p$, and at all other wavelengths, such as anti-Stokes light at wavelength $\lambda_{a-s}$. The light transmitted through filter 70 is the Stokes illumination beam $S_i$.

The Raman generator material in the Raman generator 60 can be a gas, a liquid or even a solid. Typically, a Raman generator 60 is filled with a gas, such as hydrogen or methane, under a predetermined gas pressure. Each different type of Raman generator material produces an associated Raman-shifted wavelength.

For broad band stochastic radiation, the bandwidth of the reference beam R and the Stokes source beam $S_{so}$ (the reference beam linewidth $\Delta\nu_R$) should be wide compared to the spectral width of the Raman transition of the material in the Raman generator 60 (the Raman linewidth $\Delta\nu_L$). An example of a combination of bandwidths that is appropriate for gating in hydrogen gas is a Raman linewidth $\Delta\nu_L$ of $6\times10^8$ sec$^{-1}$ and a reference beam linewidth $\Delta\nu_R$ of $4\times10^{12}$ sec$^{-1}$. It is not known precisely how wide the reference beam linewidth $\Delta\nu_R$ should be with respect to the Raman linewidth $\Delta\nu_L$ for this invention to be effective. However, it is believed that the ratio of the reference beam linewidth $\Delta\nu_R$ to the Raman linewidth $\Delta\nu_L$ is determinative of the maximum amount of contrast attainable by the imaging system 10.

Referring back to FIG. 1, the beam source 20 can include a single pass Raman generator 60 (FIG. 2), a multiple pass Raman generator cell 60 (FIG. 2), a Raman generator-amplifier 60 (FIG. 2), or an independent laser (not shown). Regardless, the wavelengths $\lambda_p$ and $\lambda_s$, must obey the relationship $(1/\lambda_p)-(1/\lambda_s)=\nu_o$, where $\lambda_o$ is the Raman shift of the material used in the Stimulated Raman amplifier 30.

The Stokes illumination beam $S_i$ is transmitted into the scattering material 17 to obtain a Stokes signal beam $S_s$. An optical train 80 transmits the Stokes illumination beam $S_i$ into the scattering material 17. The optical train 80 can be composed of one or more lenses (not shown), one or more mirrors (not shown), a fiber bundle (not shown), or a combination of these components, arranged to adjust the spatial size of the Stokes illumination beam $S_i$ so that it provides the desired illumination area at the scattering material 17. The optical train 80 can also contain filters (not shown) that can be used to adjust the intensity of the Stokes illumination beam $S_i$ at the scattering material 17 in order to meet any maximum illumination requirements that scattering material 17 may have.

It should be noted at this time that the Stokes illumination beam $S_i$ entering the scattering material 17 should preferably be collimated. The Stokes illumination beam $S_i$ propagating out of the beam source 20 should preferably be collimated. However, in the event that the Stokes illumination beam $S_i$ is not collimated at the output of the beam source 20, the optical train 80 should preferably be designed to collimate this light. Although not absolutely required for the practice of this invention, the light $S_i$ entering the scattering material 17 is preferably polarized. The output $S_i$ of the beam source 20 is generally polarized, but the optical train 80 may be designed to polarize the light $S_i$ entering the scattering material 17.

The scattering material 17, which is typically a dense scattering material, is shown in FIG. 1 with a plurality of little lines representing little scattering pieces due to the internal structure of the scattering material 17. The light that is ultimately going to form the signal light for the Stimulated Raman amplifier 30 is the light that is transmitted into or through this scattering material 17 in the least time with minimal change in polarization state. This light carries the image of interest and is the image carrying component of the Stokes source beam $S_s$. More specifically, this image carrying component is that small portion of the light emerging from the scattering material 17 that has either not been scattered within the scattering material 17 or has been scattered with minimal deviation from its original path and minimal change in polarization state. Thus, this image carrying component is that small portion of the light that comes out of the scattering material 17 first and in the least time.

The nature of this image carrying component that has been transmitted into or through the scattering material 17 without scattering or with minimal scatter and minimal alteration of polarization state depends on the thickness and nature of the material of the scattering material 17. Depending on the type of scattering material 17, this non-scattered image carrying component can be attenuated by $10^{14}$ or even more in passing through the scattering material 17. It is believed that such attenuations would be typical of the anticipated loss of light in being transmitted through about 4 centimeters of tissue, such as the human breast. It should be noted at this time that, when the scattering material 17 is live human tissue, such as the human breast, the passage of optical radiation through such human tissue will not cause any damage to that human tissue as long as the intensity of the light impinging on that human tissue is below the limit for skin damage. In contrast, examination of the breast with x-rays, as is currently done in mammography, can cause damage due to the ionizing nature of the radiation.

In addition to the image carrying component that has been transmitted through the scattering material 17 without being significantly scattered, there will be light that emerges from the scattering material 17 after it has been scattered. This light is the nonimage component and it will have been scattered over various paths (not shown) throughout the scattering material 17. It will have been scattered and spread laterally to the sides of the unscattered light. As a result, most of such scattered light will be delayed in time. Furthermore, its polarization state will be altered and it will be unpolarized and incoherent. However, there may be some component of this scattered light that is dominantly forward scattered such that it may also contribute to the image in the unscattered image carrying component.

The bulk of the scattered light that passes through the scattering material 17 (the nonimage component) will consist of light that has been sufficiently, multiply scattered so that it no longer contains any image characteristics. It will be just diffused light and all of the image information of the structure of the scattering material 17 will have been lost. This scattered light without any image characteristics comprises most of the optical energy of the light pulse that was transmitted to the scattering material 17. The exact ratio between the delayed or trailing scattered light (the nonimage component) and the leading image carrying component depends on characteristics of the scattering material 17. Exact values of this ratio are not known, but it can easily be many orders of magnitude greater than unity.

The next objective of the invention is to find that small image carrying component portion of light in front that carries the image of interest from or through scattering material 17 (the image carrying component) in the presence of the large amount of light without an image (the nonimage component) that is following along right behind the image carrying component. The nonimage component following behind the image carrying component is spread out in time. This spread in time may extend from several picoseconds to hundreds of picoseconds or even to nanoseconds. Thus, the bulk of the light energy that is transmitted through the scattering material 17 would be carried in a long scattered tail that could be spread out in time by a factor of 10–1000.

The total light emerging from the scattering material 17 is the Stokes signal beam $S_s$. As discussed above, it has a component that carries the image (the image carrying component), and a component that does not carry the image (the nonimage component). The Stokes signal beam $S_s$ emerging from the scattering material 17 need not be only light that is transmitted through the scattering material 17. It could also be light that is reflected, refracted, or otherwise affected by scattering material 17.

The Stokes signal $S_s$ emerging from the scattering material 17 passes to an optical train 90. The optical train 90 includes a sequence of two or more imaging elements, such as lenses and/or spherical mirrors (not shown), that relay the image of scattering material 17, or of a plane within the scattering material 17, which image would contain image of the object 15, if it were present. The optical train 90 can be comprised of one or more lenses (not shown), one or more mirrors (not shown), a fiber bundle (not shown), or a combination of these components.

The optical train 90 preferably includes two lenses (not shown) for relaying the image in the Stokes signal beam $S_s$. The first lens is placed one focal distance away from the plane in scattering material 17 that is to imaged. The other lens is separated by the sum of its focal length and the focal length of the first lens from the first lens. In relaying the image, the first lens essentially creates a Fourier transform of the image in its own focal plane (not shown), and the second lens creates a Fourier transform of that first transform, effectively performing a double Fourier transform to retrieve and apply the original image of the scattering material 17. The advantage of the optical train 90 performing a double Fourier transform over it performing a simple imaging operation is that the double Fourier transform operation not only relays the image, but it also reconstructs the original preferably collimated beam. The reconstructed beam is preferably as collimated as is practical in order to remove any gross optical divergence caused by any earlier optical elements, without reducing the extent to which the reconstructed beam contains optical information about the scattering material 17 and the object 15, if present. In this manner the rays of the image are more completely contained within the amplifier 30 so that they can have the full interaction along the length of the Stimulated Raman amplifier 30 (to be discussed).

A reference delay line 100 and a Stokes delay line 110 respectively responsive to reference beam R and Stokes signal beam $S_s$ produce delayed reference beam $R_d$ and delayed Stokes signal beam $S_d$, respectively. Each delay line 100 and 110 adjusts the time of transmission essentially uniformly, independent of optical characteristics such as wavelength, spectrum, polarization or coherence. It is intended that the image carrying component arriving at the stimulated Raman amplifier 30 will have a high correlation function $\rho$ (Eqn. 3) with the reference component arriving at the stimulated Raman amplifier 30. Since the correlation function p is affected by differences in transmission time, and since all transmission times in the apparatus 10 are fixed except for those through the delay lines 100 and 110, the relative delay times of delay lines 100 and 110 are adjusted so that the image carrying component arriving at the Stimulated Raman amplifier 30 will have a high correlation function $\rho$ with the reference component arriving at the Stimulated Raman amplifier 30.

The delayed Stokes signal beam $S_d$ has an image carrying component and a nonimage component, respectively responsive to the image carrying component and the nonimage component of the Stokes signal beam $S_s$, and respectively differing from the image carrying component and the nonimage component of the Stokes signal beam $S_s$, if at all, only in delay, position or propagation direction. The reference delay line 100 and the Stokes delay line 110 are adjusted so that the delayed reference beam and the second image carrying component of the delayed Stokes signal beam differ, if at all, by a preselected time-differential, by position, or by propagation direction.

An example of a reference delay line 100 is one including mirrors 115 and 120 and a retro-reflector or rooftop prism 130 that is translatable in either of the two directions shown by arrows 140. Typically, the rooftop prism 130 is mounted on a translatable stage (not shown) that is moved by a translation means (not shown), such as a screw or an electric motor. The translation means causes the translatable stage to move the rooftop prism 130 closer to (or further away from) the mirrors 115 and 120 to shorten (or lengthen) the length of the optical delay line 100.

The Stokes delay line 110 can be designed to include 2 mirrors 142, 144 and a translatable retro-reflector or rooftop prism 146. Reference delay line 100 and Stokes delay line 110 can be designed otherwise, so long as the delayed reference beam and the second image carrying component of the delayed Stokes signal beam differ by a preselected time-differential. Only the relative delay between the delayed reference beam $R_d$ and the delayed Stokes signal beam $S_d$ is significant, and so one of the delay lines, such as the Stokes delay line 110, can be a mere transmission line. Furthermore, apparatus for adjusting the relative delay between the Stokes signal and the reference beam may appear at any location in the system 10, since it is only the relative transmission time of the Stokes component and the reference component arriving at the Stimulate Raman amplifier 30 that is relevant.

Stokes polarizer 150 polarizes the delayed Stokes signal beam $S_d$ to produce a polarized Stokes signal beam $S_p$ having an image carrying component and a nonimage component responsive, respectively, to the image carrying component and a nonimage component of the delayed Stokes signal beam $S_d$. The optimal polarization of the polarized Stokes signal beam $S_p$ is such that the image carrying component of the delayed Stokes signal beam $S_d$ is unaffected by polarization, and the most optimal polarization is linear. For example, if the Stokes illumination beam $S_i$ were linearly polarized, the Stokes polarizer 150 would most preferably polarize the delayed Stokes signal beam $S_d$ linearly in the same direction as the polarization direction of the Stokes illumination beam $S_1$. The Stokes polarizer 150 according to that example blocks light which is scattered with altered polarization in the scattering material 17, but allows unscattered light carrying the image to pass. Therefore, the effect of Stokes polarizer 150 is to pass the image carrying component of the delayed Stokes signal beam $S_d$ and to substantially attenuate or block the nonimage component of the delayed Stokes signal beam $S_d$.

Reference polarizer 160 polarizes the delayed reference beam $R_d$ to produce a polarized reference beam $R_p$. If the polarized Stokes signal beam $S_i$ were linearly polarized, then the optimal reference beam polarization would be linear polarization at a direction of about 45° with respect to the direction of polarization of the polarized Stokes beam $S_p$, or alternatively, circular polarization.

A combiner 170 combines the polarized reference beam $R_p$ and the polarized Stokes signal beam $S_p$ to produce a combined beam C for input to the Stimulated Raman amplifier 30. The combined beam C has a Stokes component $S_c$ (FIG. 3(h)) with center wavelength at the Stokes wavelength $\lambda_s$ and a reference component $R_c$ (FIG. 3(a)) with center wavelength at the Raman pump wavelength $\lambda_p$, the Stokes component $S_c$ and the reference component $R_c$ being essentially collinear. The Stokes component $S_c$ is essentially unchanged with respect to the polarized Stokes signal beam $S_p$, and the reference component $R_c$ is essentially unchanged with respect to the polarized reference beam $R_p$, except for timing and propagation direction. Optical characteristics such as spectrum, polarization and coherence of the polarized Stokes signal beam $S_p$ and the polarized reference beam $R_p$ are not essentially altered by combiner 170 in producing the combined beam C. Therefore, the Stokes component $S_c$ of the combined beam C has an image carrying component $I_c$ (FIG. 3(b)) and a nonimage component $N_c$ (FIG. 3(c)), respectively responsive to the image carrying component and the nonimage component of the polarized Stokes signal beam $S_p$, and respectively differing from the image carrying component and the nonimage component of the polarized Stokes signal beam $S_p$, if at all, only in delay, position or propagation direction.

For the operation of this invention, the image carrying component $I_c$ (FIG. 3(b)) of the Stokes component $S_c$ of the combined beam C and the reference component $R_c$ (FIG. 3(a)) of the combined beam C must have high correlation $\rho(R_c, I_c)$ (Eqn. 3). For example, if the reference beam R is a pulse of relatively short duration, then the image carrying component $I_c$ and the reference component $R_c$ of the combined beam C should be overlapping. If the reference beam R is a stochastic broadband pulse, then it is a superposition of relatively short component pulses with randomly differing phases, as are the image carrying component $I_c$ and the reference component $R_c$ of the combined beam C. Each short pulse in the image carrying component $I_c$ of the Stokes component $S_c$ is overlapping with the corresponding short pulse in the reference component $R_c$. As discussed earlier, the reference delay line 100 (FIG. 1) and the Stokes delay line 110, are mutually adjusted so that the image carrying component $I_c$ and the reference component $R_c$ of the combined beam C are mutually correlated as to amplitude and phase, that is, $\rho(R_c, I_c)$ is maximized.

For the operation of this invention, the polarization state of the Stokes component $S_c$ of the combined beam differs from the polarization state of the reference component $R_c$ of the combined beam. The Stokes component $S_c$ is optimally linearly polarized, and the reference component $R_c$ is optimally linearly polarized at about 45° with respect to the linear polarization of the Stokes component $S_c$. Alternatively, the Stokes component $S_c$ is linearly polarized and the reference component $R_c$ is circularly polarized.

The combiner 170 shown in FIG. 1 is a dichroic beam splitter 170 which simultaneously reflects the polarized Stokes signal beam $S_p$ at the Stokes wavelength $\lambda_s$ and transmits the polarized reference beam $R_p$ at the Raman pump wavelength $\lambda_p$ into the Stimulated Raman amplifier 30. The combiner 170 need not be precisely as described above. For example, it could be a dichroic beam splitter (not shown) which reflects the polarized reference beam $R_p$ and transmits the polarized Stokes signal beam $S_p$.

The Stokes component $S_c$ of the combined beam C produced by the combiner 170 is polarized and has center wavelength at the Stokes wavelength $\lambda_s$. The Stokes component $S_c$ contains an image carrying component $I_c$ and a nonimage component $N_c$, both of which have the same polarization state. The image carrying component $I_c$ contains that part of the Stokes signal beam $S_s$ emerging from the scattering material 17 in the least time and with minimal alteration of polarization state. The nonimage component $N_c$ of the Stokes component $S_c$ contains that part of the Stokes signal beam $S_s$ emerging from the scattering material 17 which was scattered but has the same polarization state as the image carrying component of the Stokes component $S_c$. It follows behind the image carrying component $I_c$ of the Stokes component $S_c$ and is spread out in time.

The Stimulated Raman amplifier 30 produces an amplified output beam A responsive to the combined beam C. More specifically, the Stimulated Raman amplifier 30 amplifies that part of the combined beam C with wavelength at the Stokes wavelength $\lambda_s$ (that is, the Stokes component $S_c$) and with polarization state parallel to the polarization state of the reference component $R_c$ (that is, the part of the combined beam C with wavelength at the Raman pump wavelength $\lambda_p$). That part of the combined beam C which is so amplified is referred to as the parallel Stokes component of the combined beam C. The Stimulated Raman amplifier 30 amplifies the parallel Stokes component by a gain factor dependent on the correlation function $\rho$ (Eqn. 3) of the parallel Stokes beam and the reference component $R_c$. If that correlation function is high, the gain factor is high. If that correlation function is low, the gain factor is low and there is minimal or no amplification.

As will be explained later, the correlation function $\rho$ (Eqn. 3) with respect to the reference component $R_c$ of that part of the image carrying component $I_c$ which has its polarization state parallel to the polarization state of the reference component $R_c$ (the parallel image component $I_{pa}$ of the combined beam C shown in FIG. 3(b)) is much higher than the correlation function $\rho$ with respect to the reference component $R_c$ of that part of the nonimage component $N_c$ which has its polarization state parallel to the polarization state of the reference component $R_c$ (the parallel nonimage component $N_{pa}$ of the combined beam C as shown in FIG. 3(c)). Only the parallel image component $I_{pa}$ will experience gain while the reference component $R_c$ is present. The remaining part of the parallel Stokes component, the parallel nonimage component $N_{pa}$ which arrives at the Stimulated Raman amplifier 30 after the reference component $R_c$, does not carry an image because of multiple path scattering within the scattering material 17. This scattered light will not be amplified by the Stimulated Raman amplifier 30 as much as the parallel image component $I_{pa}$ because, when it does arrive at the Stimulated Raman amplifier 30, it does not correlate as well with the reference component $R_c$.

If the reference beam R is a relatively short duration coherent pulse, then the correlation function $\rho$ (Eqn. 3) translates to overlapping. The parallel image component $I_{pa}$ will be amplified because it is present as a pulse in the Stimulated Raman amplifier 30 at the same time as the pulse in the reference component $R_c$, and therefore has a high correlation. The parallel nonimage component $N_{pa}$ will not be amplified because it was delayed, and is present in the Stimulated Raman amplifier 30 only when there is no pulse in the reference component $R_c$, and so it has a low correlation $\rho(R_c, N_{pa})$.

If the reference beam R is a stochastic broadband pulse, then it is a superposition of relatively short component pulses with randomly varying phases, as are the image carrying component $I_c$ and the reference component $R_c$ of the combined beam C. Each short pulse in the image carrying component $I_c$ of the Stokes component $S_c$ is overlapping with the corresponding short pulse in the reference component $R_c$. Therefore, the parallel image component $I_{pa}$ and the reference component $R_c$ have a high correlation $\rho(R_c, I_{pa})$, and so the parallel image component $I_{pa}$ will be amplified. On the other hand, the parallel nonimage component $N_{pa}$ and the reference component $R_c$ would not have a high correlation $\rho(R_c, N_{pa})$ because, although they might overlap, each temporal component in the parallel nonimage component $N_{pa}$ would not match in amplitude and phase the corresponding temporal component in the reference component $R_c$. Therefore, the parallel nonimage component $N_{pa}$ would not be amplified by as high a gain factor as the parallel image component $I_{pa}$.

Referring now to FIGS. 3(a)-3(h), the effect of the Stimulated Raman amplifier 30 on the polarization states of the combined beam C is shown for the optimal polarization state of the combined beam C, in which the reference component $R_c$ and the Stokes component $S_c$ (including the image carrying component $I_c$ and the nonimage component $N_c$) are linearly polarized at 45° with respect to each other.

FIG. 3(a) shows the polarization state of the reference component $R_c$ of the combined beam C. FIG. 3(h) shows the polarization state of the Stokes component $S_c$ of the combined beam C. FIG. 3(b) shows the polarization state of the image component $I_c$ of the Stokes component $S_c$, the image component $I_c$ being resolved into parallel and perpendicular image components $I_{pa}$ and $I_p$, respectively, being parallel and perpendicular, respectively, to the reference component $R_c$. FIG. 3(c) shows the polarization state of the nonimage component $N_c$ of the Stokes component $S_c$, the nonimage component $N_c$ being resolved into parallel and perpendicular nonimage components $N_{pa}$ and $N_p$, respectively, being parallel and perpendicular, respectively, to the reference component $R_c$. The image component $I_c$ and the nonimage component $N_c$, which together constitute the Stokes component $S_c$, have the same polarization state and the same center wavelength, the Stokes wavelength $\lambda_s$.

The Stimulated Raman amplifier 30 operates on the image component $I_c$ of the Stokes component $S_c$ to produce the image component $I_{out}$ of the amplified signal output beam A. The parallel image component $I_{pa}$ is amplified (not to scale) because it has polarization state parallel to that of the reference beam $R_c$, high correlation $\rho(R_c, I_{pa})$ (Eqn. 3), and center wavelength at the Stokes wavelength $\lambda_s$. The perpendicular component $I_p$ is not significantly amplified because its polarization state does not have an appreciable component parallel to the polarization state of the reference component $R_c$. Therefore, the polarization state of the image output component $I_{out}$ is different than the polarization state of the image carrying component $I_c$.

The Stimulated Raman amplifier 30 operates on the nonimage component $N_c$ (FIG. 3(c)) of the Stokes component $S_c$ to produce the nonimage component $N_{out}$ (FIG. 3(e)) of the amplified signal output beam A. The perpendicular nonimage component $N_p$ is not significantly amplified because its polarization state does not have an appreciable component parallel to the polarization state of the reference component $R_c$. However, even that parallel nonimage component $N_{pa}$ with polarization state parallel to the polarization state of the reference component $R_c$ is not substantially amplified relative to amplification of the parallel image component $I_{pa}$ because of relatively low correlation $\rho(R_c, N_{pa})$ (Eqn. 3). If the reference beam R is in the form of a relatively short pulse, the parallel nonimage component $N_{pa}$ is essentially unamplified by the Stimulated Raman amplifier 30. If the reference beam R is in the form of a relatively long broad band stochastic pulse, the Stimulated Raman amplifier 30 would not amplify this component by any appreciable gain factor when compared with amplification of the parallel image component $I_{pa}$, because of a much smaller correlation function $\rho$ with respect to the reference component $R_c$. Thus, the polarization state of the output nonimage component $N_{out}$ is essentially the same as the polarization state of the nonimage component $N_c$ of the Stokes component $S_c$.

FIG. 3(f) shows the polarization state of the image component $I_{out}$ of FIG. 3(d) resolved into components parallel and perpendicular to the polarization state of the Stokes component $S_c$. Output image component $I_{out}$ has a substantial component with polarization state perpendicular to the polarization state of the Stokes component $S_c$.

FIG. 3(g) shows the polarization state of the nonimage component $N_{out}$ of FIG. 3(d) resolved into components parallel and perpendicular to the polarization state of the Stokes component $S_c$. That component, if any, of the polarization state of the output nonimage component $N_{out}$, which is perpendicular to the polarization state of the Stokes component $S_c$ is relatively weak relative to the component of the output image beam $I_{out}$ with polarization state perpendicular to the Stokes beam $S_c$ polarization state.

Stimulated Raman amplifier 30 (FIG. 1) includes a cell capable of transmitting signals at both the Raman pump wavelength $\lambda_p$ and the Stokes wavelength $\lambda_s$, and it contains a Raman material (not shown) that produces Stimulated Raman amplification of the parallel Stokes component when that material is pumped by the reference component $R_c$. The gain factor for such Stimulated Raman amplification depends on the correlation function $\rho$ (Eqn. 3) of the parallel Stokes component and the reference component $R_c$. In order to have maximum gain in the Stimulated Raman amplifier 30, the wavelength of the parallel Stokes component and the wavelength of the reference component $R_c$ must be separated by the frequency shift of the Raman material in the Stimulated Raman amplifier 30. The most reliable way to accomplish this is to fill the Raman generator 60 (FIG. 2) and the Stimulated Raman amplifier 30 with the same Raman material having the same physical properties (and at the same pressure/density, if that Raman material is a fluid). If the Raman material is a gas, such as hydrogen, the Raman material in the Raman generator 60 and the Raman material in the Stimulated Raman amplifier 30 could be drawn from the same gas supply and connected together to provide for equilibration.

For a relatively short pulse reference beam R, the amplification factor or gain of the Stimulated Raman amplifier 30 is determined by the energy density or power in the reference component, with a typical value of the order of $10^{10}$. The gain will be less for relatively long pulse broad bandwidth stochastic radiation reference beam R. For a relatively short pulse reference beam R, the amplification factor or gain also determines the contrast between the amplified signal pulse image in the output image component $I_{out}$ and the delayed scattered light in the output nonimage component $N_{out}$ that comes after the amplified image. For a relatively long pulse broad bandwidth stochastic radiation reference beam R, the contrast between the output image component $I_{out}$ and the output nonimage component $N_{out}$ is determined by the value of the correlation function $\rho(R, N_{out})$ (Eqn. 3).

Basically, as indicated above (FIGS. 3(a)-3(h)), it is the purpose of the Stimulated Raman amplifier 30 to amplify and/or alter the polarization state of image component $I_c$ relative to the nonimage component $N_c$ so that the component of the output image component $I_{out}$ with polarization state perpendicular to the Stokes component $S_c$ polarization state has greater energy than that of the component of the output nonimage component $I_{out}$ with polarization state perpendicular to the Stokes component $S_c$ polarization state. The Stimulated Raman amplifier 30 accomplishes these objectives by amplifying the image component $I_c$ more than the nonimage component $N_c$, and so that the polarization state of the output image component $I_{out}$ has a significant component perpendicular to the polarization state of the Stokes component $S_c$ but the polarization state of the output nonimage component $N_{out}$ does not have a significant component perpendicular to the polarization state of the Stokes component $S_c$. For relatively short pulse reference beam R, the desired effect is attained primarily through amplification; for relatively long broad bandwidth stochastic reference beam R, the desired effect is attained primarily through affecting the polarization state.

Referring back to FIG. 1, the amplified output beam A passes through an output filter 175 that passes that part of the amplified output beam A at or near the Stokes wavelength $\lambda_s$ and blocks all other wavelengths. The output filter 175 serves to block the reference component $R_c$ which passed through the Stimulated Raman amplifier 30. The light then goes to output polarizer 180 which is oriented to pass light with polarization state perpendicular to the polarization state of the Stokes component $S_C$ and to block light with polarization state parallel to the polarization state of the Stokes component $S_C$. The output polarizer 180 thus blocks the Stokes component which directly passed through the Stimulated Raman Amplifier 30, and most importantly, most of the nonimage component $N_{out}$ (FIG. 3) of the output beam O, since neither of these components have appreciable components with polarization state perpendicular to the Stokes component $S_C$. Virtually the only part of the amplified output beam A that passes through the output polarizer 180 is the output image component $I_{out}$ (FIG. 3), since that component has an appreciable component with polarization state perpendicular to the polarization state of the Stokes component $S_C$.

As a numerical example, assume that the reference beam R is a relatively short pulse and that the Stimulated Raman amplifier 30 has a gain of $10^{9}$ and that the energy in the scattered light portion of the Stokes light that is transmitted through the sample 19 is $10^8$ greater than the energy in the image-bearing signal pulse. Therefore, of all of the Stokes light that is transmitted through the scattering material 17, only a very small fraction of such light, corresponding to $10^{-8}$ of it (or one part in $10^8$), carries the image. Obviously, such a low level of light cannot be seen with the human eye or even with the world's most sensitive camera, because it would be swamped by the background scattered light. However, after the Stokes light passes through the gated Stimulated Raman amplifier 30, the image or signal pulse is amplified by $10^9$, and the background scattered light is not appreciably amplified. As a result, at the output of the Stimulated Raman amplifier 30 the amplified signal pulse now has 10 times as much energy as all of the unamplified scattered light.

The output from the output polarizer 180 then goes through an output optical train 185 which relays or reimages the image from the scattering material 17 and sends it to a detector 190. The detector 190 includes a two-dimensional, spatially-resolved detector, such as a charge coupled device (CCD) camera, which is capable of detecting the image and either displaying it directly or transferring it to suitable recording and processing equipment. The detector 190 must have sufficient sensitivity to respond to the energy of the signal at the output of the output optical train 185, should be capable of integrating multiple, amplified Stokes signal pulses, and should have a noise level that allows it to be used with signal levels near the quantum limit, that is, capable of detecting single photons.

The contrast of imaging apparatus 10 is determined by many factors, including the stimulated Raman Amplifier 30 power the leakage of the wrong polarization through polarizers 150, 160 and 180, the nature of the object 15 and scattering material 17, and the nature of the beam source 20. Furthermore, an extinction of greater than 10,000 ($10^4$) can be achieved with the polarizers 150, 160 and 180, and so the power requirements for the stimulated Raman Amplifier 30 are reduced. In the example discussed above, it was pointed out that if the nonimage component of the Stokes signal beam were a factor of $10^8$ greater than the image component of the Stokes signal, then stimulated Raman Amplifier 30 amplification by a gain factor of $10^9$ would produce an amplified output beam A in which the image component $I_{out}$ were $10\times$ greater than the nonimage component $N_{out}$. However, because polarizers 150, 160 and 180 can reduce the nonimage component by a factor of $10^4$, amplification by a stimulated Raman Amplifier 30 gain factor of $10^5$ would suffice to provide an image component $I_{out}$ to nonimage component $N_{out}$ ratio of 10.

At this point it should be noted that the wavelength $\lambda_s$ of the Stokes illumination beam $S_i$ and the pulse width of the reference beam R are chosen based on the characteristics of the scattering material 17, and the Raman pump wavelength $\lambda_p$ of the reference beam R is chosen based on the type of Raman material contained in the Raman generator 60.

Consider the example in which the scattering material 17 is live human tissue, such as a human breast. In this case, the Stokes illumination beam $S_i$ would preferably have a wavelength of about 850 nm, which would therefore be the Stokes wavelength $\lambda_s$. The Raman pump wavelength $\lambda_p$, the wavelength of the reference beam R, would have to be shorter than this Stokes wavelength $\lambda_s$ of 850 nm, because the Raman generator 60 produces light that is shifted to a longer wavelength from the Raman pump wavelength $\lambda_p$, by an amount corresponding to the Raman shift of the Raman material in the Raman generator 60. If the Raman material in Raman generator 60 were selected to be, for example, hydrogen gas at a preselected pressure, and a Stokes wavelength $\lambda_s$ were desired, then the beam source 20 would need to produce reference beam R at a Raman pump wavelength $\lambda_p$ of 628 nm.

Several specific alternatives to the above described embodiment will now be discussed. In one embodiment, optical train 90 performs an optical Fourier transform of the Stokes signal beam $S_s$ from the scattering sample M, and then relays that Fourier transformed Stokes light to the stimulated Raman Amplifier 30 by way of the Stokes delay line 110, the Stokes polarizer 150, and the combiner 170. The stimulated Raman Amplifier 30 then amplifies in space the Fourier transformed Stokes light. Since the Stimulated Raman Amplifier 30 amplifies a Fourier transform and not an image, the output optical train 185 responsive to the output from output polarizer 180 takes another Fourier transform of the Fourier transformed image in order to reconstruct the image of the original scattering material 17, or a place within that scattering material 17, which is then relayed to the detector 190. The output optical train 185 can be a simple lens or a high quality camera lens, but its separation from the stimulated Raman Amplifier 30 and the detector 190 is readjusted so that the function of the output optical train 185 is to form a Fourier transform of light from the stimulated Raman Amplifier 30 rather than forming an image of light from the stimulated Raman Amplifier 30. This embodiment offers an improved signal-to-noise ratio in the amplified image because it does not require exact matching of the structure in the image to the amplifier Fresnel number for minimum noise.

In another embodiment, the Stokes illumination beam $S_i$ is a relatively short pulse. A stretcher (not shown) stretches the pulse for illumination into the scattering material 17, and a pulse compressor (not shown) compresses the Stokes signal beam $S_s$ emerging from the scattering material 17. This embodiment combines the high contrast inherent in short pulse gates while permitting the use of with long pulses needed to reduce sample intensity.

It is understood that many other changes and additional modifications of the invention are possible in view of the teachings herein without departing from the scope of the invention as defined in the appended claims.

What is claimed is:

1. An apparatus for imaging into or through a scattering material, said apparatus comprising:
   (a) a source for producing a broadband reference beam and a Stokes illumination beam, the Stokes illumination beam being transmitted into the scattering material to produce a Stokes signal beam at the output of the scattering material, the broadband reference beam having a center wavelength at a preselected Raman pump wavelength, the Stokes illumination beam having a center wavelength at a preselected Stokes wavelength and being correlated to the reference beam, and the Stokes signal beam having a first image carrying component and a first nonimage component;
   (b) means responsive to the Stokes signal beam for producing a polarized Stokes signal beam, the polarized Stokes signal beam having a polarized image carrying component and having a polarized nonimage component;
   (c) means for polarizing the reference beam to produce a polarized reference beam;
   (d) means for combining the polarized reference beam and the polarized Stokes signal beam to produce a combined beam having a Stokes component with center wavelength at the Stokes wavelength and having a reference component with center wavelength at the Raman pump wavelength, the Stokes component having a second image carrying component and a second nonimage component, so that the second image carrying component and the reference component are mutually correlated, and so that the polarization state of the Stokes component differs from the polarization state of the reference component;
   (e) a Stimulated Raman amplifier responsive to the combined beam for producing an amplified signal beam having a third image carrying component with polarization state perpendicular to the polarization state of the Stokes component and having a third nonimage component with polarization state substantially parallel to the polarization state of the Stokes component;
   (f) means for polarizing the amplified signal beam to produce a polarized output beam with polarization state essentially perpendicular to the polarization state of the Stokes component; and
   (g) means responsive to the polarized output beam for detecting the third image carrying component.

2. The apparatus according to claim 1 further comprising means for adjusting the relative delay time of the Stokes signal beam with respect to the reference beam.

3. The apparatus according to claim 1 wherein said source comprises:
   a pulse laser for producing a source beam;
   means responsive to the source beam for producing the reference beam and a Stokes source beam; and
   means responsive to the Stokes source beam for generating the Stokes illumination beam.

4. The apparatus according to claim 3 wherein said pulse laser produces the source beam having a short pulse.

5. The apparatus according to claim 3 wherein said pulse laser produces the source beam pulse having short coherence.

6. The apparatus according to claim 1 further comprising means for polarizing the Stokes illumination beam.

7. The apparatus according to claim 6 further comprising means for linearly polarizing the Stokes illumination beam.

8. The apparatus according to claim 1 wherein:
said source of limitation (a) comprises a Raman generator using Raman generator material;
said Stimulated Raman amplifier of limitation (e) uses Raman amplifier material; and
said Raman amplifier material is substantially the same material with substantially the same physical properties as said Raman generator material.

9. The apparatus according to claim 8 wherein:
said Raman generator material is a gas drawn from a gas supply; and
said Raman amplifier material is a gas drawn from said gas supply.

10. The apparatus according to claim 9 wherein said generator gas is hydrogen.

11. The apparatus according to claim 1 wherein the polarization means of limitation (b) further comprises means for linearly polarizing the Stokes signal beam to produce the polarized Stokes signal beam.

12. The apparatus according to claim 11 wherein the polarization means of limitation (c) further comprises means for linearly polarizing the reference beam to produce the polarized reference beam so that the polarized reference beam is linearly polarized at
    45° with respect to the polarized Stokes signal beam.

13. The apparatus according to claim 11 wherein the polarization means of limitation (c) further comprises means for polarizing the reference beam to produce the polarized reference beam so that the polarized reference beam is circularly polarized.

14. The system according to claim 1 wherein the Stimulated Raman amplifier of limitation (e) amplifies the component of the Stokes component with polarization state parallel to the polarization state of the reference component by a gain factor dependent on the correlation of the component of the Stokes component with polarization state parallel to the polarization state of the reference component with the reference component.

* * * * *